(12) United States Patent
Hatto

(10) Patent No.: US 9,968,476 B2
(45) Date of Patent: May 15, 2018

(54) ARM SLING AND METHOD OF FORMING THE SAME

(71) Applicant: Melanie Deborah Hatto, Cape Coral, FL (US)

(72) Inventor: Melanie Deborah Hatto, Cape Coral, FL (US)

( * ) Notice: Subject to any disclaimer, the term of this patent is extended or adjusted under 35 U.S.C. 154(b) by 41 days.

(21) Appl. No.: 15/171,069

(22) Filed: Jun. 2, 2016

(65) Prior Publication Data
US 2017/0348135 A1    Dec. 7, 2017

(51) Int. Cl.
*A61F 5/00*     (2006.01)
*A61F 5/37*     (2006.01)
*A61F 5/30*     (2006.01)

(52) U.S. Cl.
CPC .............. *A61F 5/3738* (2013.01); *A61F 5/30* (2013.01)

(58) Field of Classification Search
CPC .................................................... A61F 5/3738
USPC ............................................................. 602/4
See application file for complete search history.

(56) References Cited

U.S. PATENT DOCUMENTS

| | | | | |
|---|---|---|---|---|
| 1,396,270 A | * | 11/1921 | Grierson ............... | F41C 33/001 224/150 |
| 1,490,066 A | * | 4/1924 | Carr ........................ | A45F 3/14 182/3 |
| 1,490,381 A | * | 4/1924 | Gobar ................... | A61F 5/3738 602/4 |
| 2,446,197 A | * | 8/1948 | Sloan ..................... | F41C 33/001 224/150 |
| 2,543,847 A | * | 3/1951 | Hallstedt .................. | A61H 3/00 602/4 |
| 2,576,559 A | * | 11/1951 | Bennek ................. | F41C 33/002 224/149 |
| 2,616,419 A | * | 11/1952 | Karfiol .................. | A61F 5/3738 602/4 |
| 2,812,123 A | * | 11/1957 | Girton .................. | A47D 13/086 224/150 |
| 3,554,194 A | * | 1/1971 | Johnson ............... | A61F 5/3738 602/4 |
| 3,706,310 A | * | 12/1972 | Garnett ................ | A61F 5/3738 128/DIG. 15 |
| 4,601,161 A | * | 7/1986 | Drellich .................. | B68B 1/00 54/46.1 |
| 4,815,639 A | * | 3/1989 | Lehman ............... | A47D 13/025 224/159 |
| 5,056,253 A | * | 10/1991 | Willumsen .............. | F41C 27/22 42/94 |
| 5,165,584 A | * | 11/1992 | Meagher ................. | A45F 3/14 124/88 |
| 5,518,486 A | * | 5/1996 | Sheeler .............. | A63B 21/0004 482/131 |

(Continued)

*Primary Examiner* — Kristen Matter
(74) *Attorney, Agent, or Firm* — Jetter & Associates, P.A.

(57) ABSTRACT

An arm sling includes a flat, elongated strap having a first end and a second end; a ring structure attached to the first end; and a double loop structure having a first loop and a second loop. The second end can extend through the first loop structure, then through the second loop structure, then back through the second loop structure, then through the first loop structure to define an arm loop and a remaining portion of the strap between the double loop structure and the second end. The second end can extend through the ring structure and attach to the remaining portion via an attachment element to define a shoulder loop.

12 Claims, 2 Drawing Sheets

(56) References Cited

U.S. PATENT DOCUMENTS

| | | | | |
|---|---|---|---|---|
| 6,095,993 | A * | 8/2000 | Hawkins | A61F 5/3738 602/4 |
| 8,196,588 | B1 * | 6/2012 | Krenzel | A61F 5/3738 128/869 |
| 2001/0046904 | A1 * | 11/2001 | Arvanitis, Jr. | A63B 69/0059 473/208 |
| 2007/0129657 | A1 * | 6/2007 | Fisher | A61F 5/3738 602/4 |
| 2011/0306477 | A1 * | 12/2011 | Keen | A63B 21/02 482/122 |
| 2014/0203054 | A1 * | 7/2014 | Dove | F41C 33/001 224/257 |

* cited by examiner

ARM SLING AND METHOD OF FORMING THE SAME

FIELD OF THE INVENTION

The present invention related to medical devices, and more particularly, to rehabilitative arm slings.

BACKGROUND OF THE INVENTION

Within the medical and physical therapy fields, arm slings have been used to immobilize a wearer's arm or shoulder due to various types of injuries to assist with healing processes.

Developments in the arm sling art have produced arm slings having increased complexities and cost.

SUMMARY OF THE INVENTION

The present invention provides an arm sling that can immobilize a wearer's arm or shoulder for rehabilitative purposes.

In an exemplary embodiment of the present invention, an arm sling can include a flat elongated strap having a first end and a second end; a ring structure attached to the first end; and a double loop structure having a first loop and a second loop.

In an exemplary aspect of the invention, the second end can extends through the first loop structure, then through the second loop structure; and then back through the second loop structure, then through the first loop structure to define an arm loop and a remaining portion of said strap between said double loop structure and the second end.

In another exemplary aspect, the second end can then extend through the ring structure and attach to the remaining portion via an attachment element to define a shoulder loop.

In a further exemplary aspect, the strap can be formed of an elastomeric material.

In still a further exemplary aspect, the attachment element can include a hook and loop structure.

In yet another exemplary aspect, the shoulder loop can be larger than the arm loop.

In another exemplary aspect, an arm sling can further include a pad attached to the shoulder loop, with the pad optionally being provided with a cylindrical shape and/or optionally being slidably attached to the shoulder loop.

According to another exemplary embodiment, a method of forming an arm sling, can include the following steps: providing a flat elongated strap having a first end and a second end; providing a ring structure attached to the first end; providing a double loop structure having a first loop and a second loop; feeding the second end through the first loop structure, then through the second loop structure, and then back through the second, then through the first loop structure to form an arm loop and define a remaining portion of the strap; feeding the second end through the ring structure; and attaching the second end to the remaining portion to form a shoulder loop.

In a further exemplary aspect, the strap can be formed of an elastomeric material.

In still a further exemplary aspect, the attachment element can include a hook and loop structure.

In yet another exemplary aspect, the shoulder loop can be larger than the arm loop.

In another exemplary aspect, a method of forming an arm sling can further include attaching a pad to the shoulder loop.

In still another exemplary aspect, a pad can optionally be provided with a cylindrical shape and/or optionally be slidably attached to the shoulder loop.

These and other exemplary aspects are described herein.

DETAILED DESCRIPTION

An object of the present invention is to provide an arm sling.

Another object of the present invention is to provide a method of forming an arm sling.

These and other objects are expressly and apparently provided via the illustrative embodiments and aspects described herein.

It should be noted that this disclosure includes a plurality of embodiments, each having a plurality of elements and/or aspects, and such elements and/or aspects need not necessarily be interpreted as being conjunctively required by one or more embodiments of the present invention. Rather, all combinations of all elements and/or aspects described herein can enable a separate embodiment of the present invention, which may be claimed with particularity in one or more future filed Non-Provisional Patent Applications. Moreover, any particular structure, arrangement, and/or functional logic disclosed herein, whether expressly or implicitly, are to be construed strictly as illustrative and enabling, and not necessarily limiting. Therefore, it is expressly set forth that such structure, arrangement, and functional logic, independently or in any combination of one of more thereof, are merely illustratively representative of one or more elements and/or aspects of one or more embodiments of the present invention and are not to be construed as necessary in a strict sense.

Further, to the extent the same element or aspect is defined differently anywhere within this disclosure, whether expressly or implicitly, the broader definition is to take absolute precedence, with the distinctions encompassed by the narrower definition to be strictly construed as optional.

Illustratively, perceived benefits of the present invention can include functional utility, whether expressly or implicitly stated herein, or apparent herefrom. However, it is expressly set forth that these benefits are not intended as exclusive. Therefore, any explicit, implicit, or apparent benefit from the disclosure herein is expressly deemed as applicable to the present invention.

Figure 1:
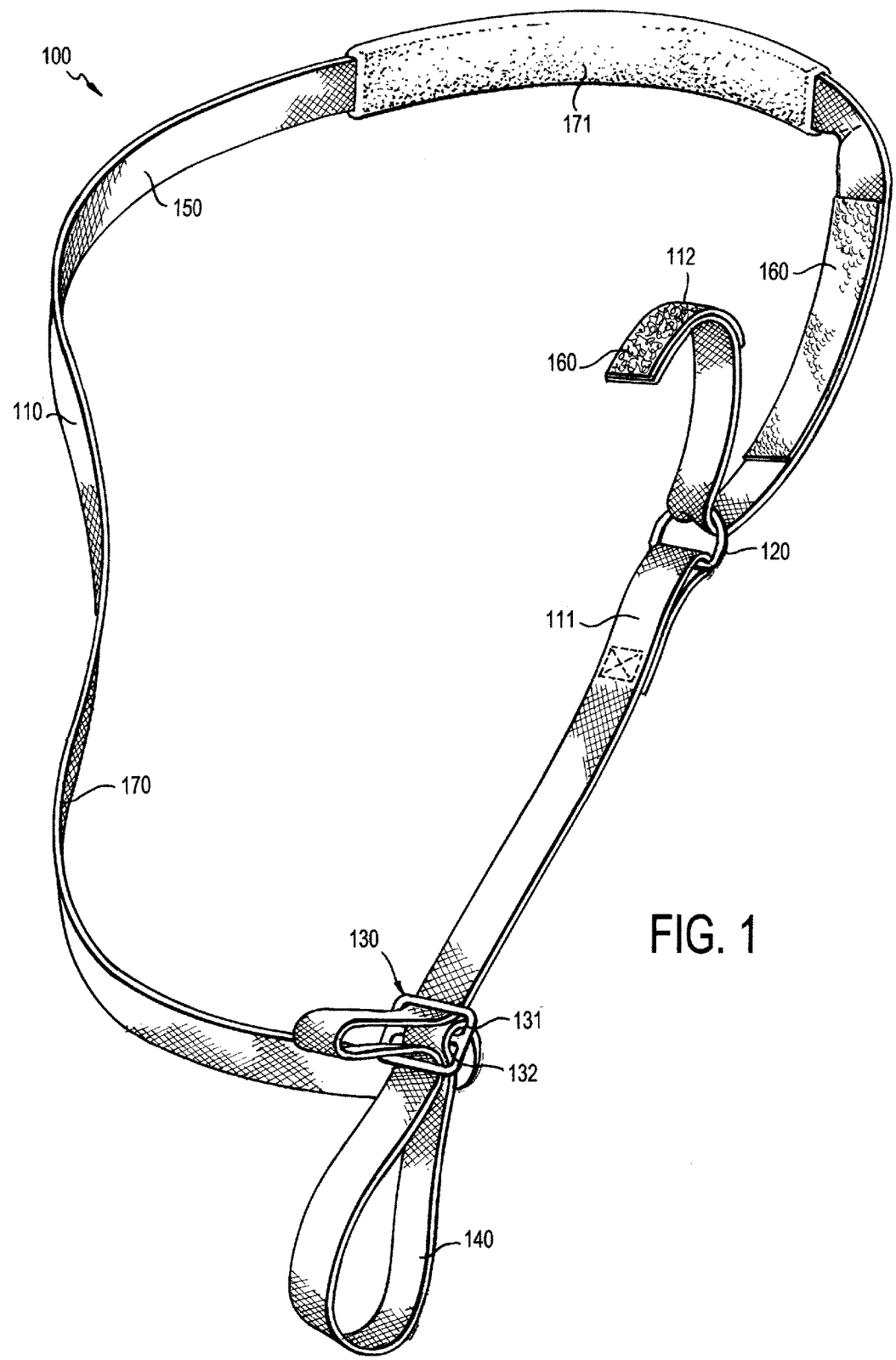
FIG. 1 illustrates an exemplary embodiment of an arm sling according to present invention.

FIG. 1 illustrates an exemplary arm sling according to the present invention, in which such an arm sling 100 can include a flat, elongated strap 110, a ring structure 120, and a double loop structure 130.

In an exemplary aspect of the present invention, strap 110 can be formed from any desired one or more materials that are functional compatibility with the present invention as described. For example and not in limitation, strap 110 can be formed from any one or more of cotton, nylon, rubber, plastic, polypropylene, leather, naturally-occurring material, man-made material, etc., and can optionally be formed from an elastic material to facilitate use and/or comfort.

In another exemplary aspect, ring structure 120 can be provided with any one or more functionally compatible materials (e.g., metallic, rubber, plastic, wood, crystalline, man-made, naturally-occurring, etc.) and/or shapes (e.g, geometric, symmetric, asymmetric, continuous, discontinuous, etc.) desired. As illustratively shown, ring structure 120 can be provided as a "D-Ring" having a "D" shape, however, any other one or more geometrics can be provided, including ones having a continuous or discontinuous shape, such as a "C" shape, for example and not in limitation, insofar as functionally consistent with the present invention.

In a further exemplary aspect, as with ring structure 120, double loop structure 130 can also be provided with any one or more functionally compatible materials and/or shapes desired. As illustratively shown, double loop structure 130 can be provided with a structure having a first loop 131 and a second loop 132, each of which being configured to allow strap 110 to pass therethough at least twice.

As further illustrated in FIG. 1, second end 112 can extend through first loop 131, then through second loop 132. Next, while leaving an excess amount of strap 110 at second end 112, which forms arm loop 140, second end 112 can extend back through second loop 132, and then back through first loop 131 to define a remaining portion 150 of the strap from first loop 131 to second end 112.

As additionally illustrated, second end 112 can then extend through ring structure 120 and attach to remaining portion 150 via attachment element 160 to form shoulder loop 170, which can be larger than arm loop 140. In an exemplary aspect, attachment element 160 can provided as any one or more structures configurable to attach second end 112 to remaining portion 150, including, for example and not in limitation, one or more of a button, buckle, a hook and loop fastener, a first magnetic element and a second magnetic or ferromagnetic element, a snap, a hook, a clasp, etc. As illustratively shown in FIG. 1, attachment element 160 can be respectively provided on second end 112 and remaining portion 150 as a hook and loop combination, which can securably engage the second end to the remaining portion.

As additionally illustrated in FIG. 1, sling 100 can optionally include a pad 171, which can be attached in any desired manner (e.g., stitching, adhesive, static friction, loop and hook, etc.) to strap 110 to provide a cushioning function for a wearer of the sling. In an exemplary aspect, as with strap 110, pad 171 can be formed from any material desired, and can optionally include a foam or other cushioning material. In one exemplary embodiment, pad 171 can be provided with a cylindrical shape, and surround and conform to the shape of strap 110, which can allow the pad to be slidable attached thereto so as to allow a user to move the pad to an optimal position.

Figure 2:
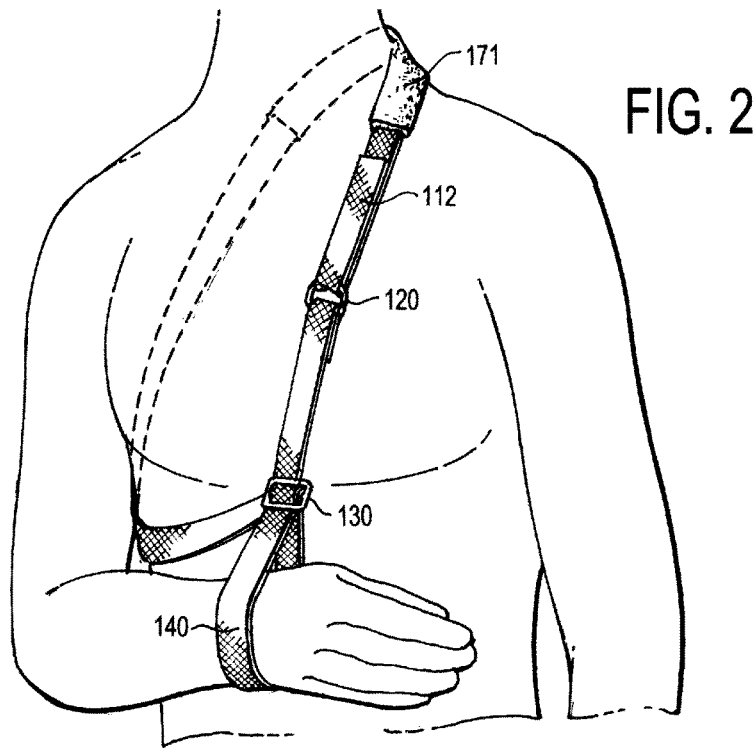
FIG. 2 illustrates an exemplary arm sling worn by a user.

FIG. 2 illustrates an exemplary arm sling worn by a user, with arm loop 140, being worn around the user's arm or wrist, and shoulder loop 170, being worn around the user's shoulder, cooperatively assisting in desired immobilization of the user's arm and/or shoulder.

Figure 3:
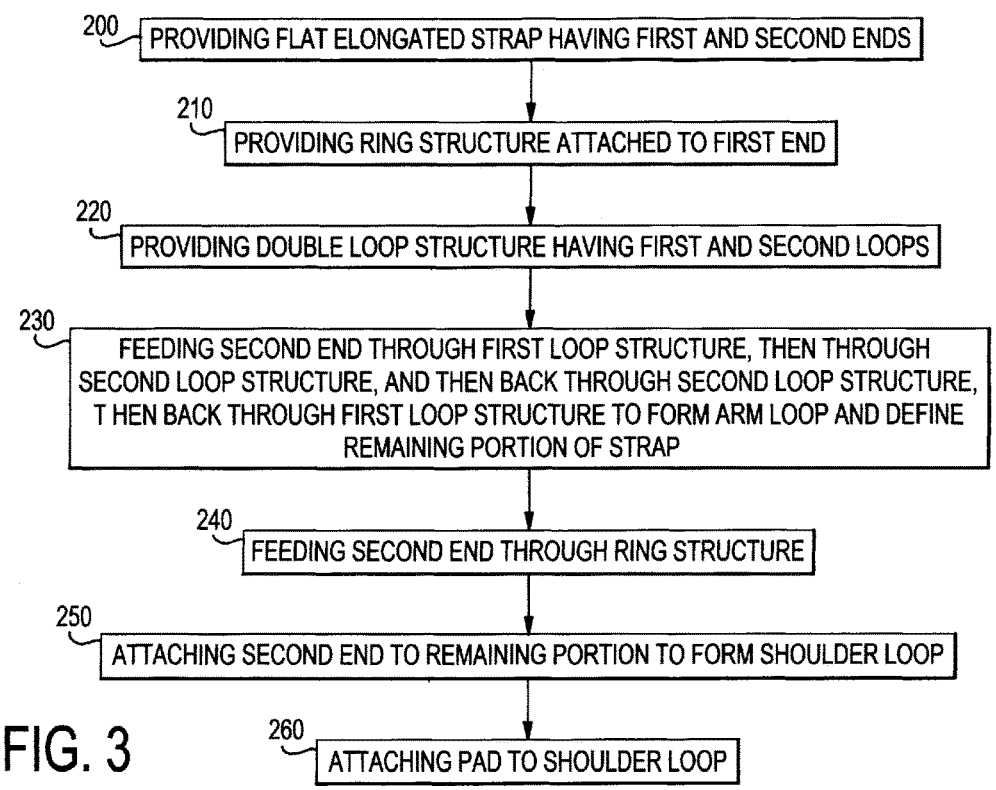
FIG. 3 illustrates exemplary method steps according to an exemplary embodiment of the invention.

FIG. 3 illustrates an exemplary method of forming an arm sling according to the present invention, and can include the following: providing a flat elongated strap 110 having first and second ends 111, 112 (step 200); providing a ring structure 120 attached to the first end (step 210); providing a double loop structure 130 having first and second loops 131, 132 (step 220); feeding the second end through the first loop structure, then through the second loop structure, and then back through the second loop structure, then back through the first loop structure to form arm loop 140 and a remaining portion 150 of the strap (step 230); feeding the second end through the ring structure (step 240); attaching the second end to the remaining portion to form a shoulder loop 170 (step 250); and optionally, attaching a pad 171 to the shoulder loop (step 260).

Notably, the optional attaching step (step 260) can generally be effectuated at any point after the step of providing strap 110. Further, the remaining steps can be effectuated in any functionally compatible order, including feeding first end 111 through any element of the present invention, such as first and second loops 131, 132 for example and not in limitation.

It will be apparent to one of ordinary skill in the art that the manner of making and using the claimed invention has been adequately disclosed in the above-written description of the exemplary embodiments, aspects, and steps of the present invention.

It should be understood, however, that the invention is not necessarily limited to the specific embodiments, aspects, steps, order, arrangement, and components shown and described above, but may be susceptible to numerous variations within the scope of the invention, with such variations deemed within the spirit of the present invention. For example, while elements of the present invention have been illustratively shown having particular shapes, it should be understood that the same can be provided with any one or more geometric shapes, including irregular shapes and ones having continuous or discontinuous portions, insofar as the resulting elements are functionally consistent with the present invention.

Therefore, the specification and drawings are to be regarded in an illustrative and enabling, rather than a restrictive, sense.

Accordingly, it will be understood that the above description of the embodiments of the present invention are susceptible to various modifications, changes, and adaptations, and the same are intended to be comprehended within the meaning and range of equivalents apparent to one of ordinary skill in the art.

Therefore I claim:

1. An arm sling, comprising:
   an elongated strap having a first end and a second end;
   a ring structure attached to the first end; and
   a double loop structure having a first loop structure and a second loop structure; wherein the second end extends through the first loop structure, then through the second loop structure, then back through the second loop structure, then through the first loop structure to define an arm loop and a remaining portion of said strap between said double loop structure and the second end, and the second end extends through said ring structure and attaches to the remaining portion via an attachment element to define a shoulder loop.

2. The arm sling of claim 1, wherein said strap is formed of an elastomeric material.

3. The arm sling of claim 1, wherein the attachment element includes a hook and loop structure.

4. The arm sling of claim 1, wherein the shoulder loop is larger than the arm loop.

5. The arm sling of claim 1, further comprising a pad attached to the shoulder loop.

6. The arm sling of claim 5, wherein the pad is provided with a cylindrical shape, and the pad is slidably attached to the shoulder loop.

7. A method of forming an arm sling, comprising:
   providing an elongated strap having a first end and a second end;
   providing a ring structure attached to the first end;

providing a double loop structure having a first loop structure and a second loop structure;

feeding the second end through the first loop structure, then through the second loop structure, and then back through the second loop structure, then through the first loop structure to form an arm loop and define a remaining portion of the strap;

feeding the second end through the ring structure; and attaching the second end to the remaining portion via an attachment element to form a shoulder loop.

8. The method of claim 7, wherein said strap is formed of an elastomeric material.

9. The method of claim 7, wherein the attachment element includes a hook and loop structure.

10. The method of claim 7, wherein the shoulder loop is larger than the arm loop.

11. The method of claim 7, further comprising attaching a pad to the shoulder loop.

12. The method of claim 11, wherein the pad is provided with a cylindrical shape, and the pad is slidably attached to the shoulder loop.

\* \* \* \* \*